Figure 1:
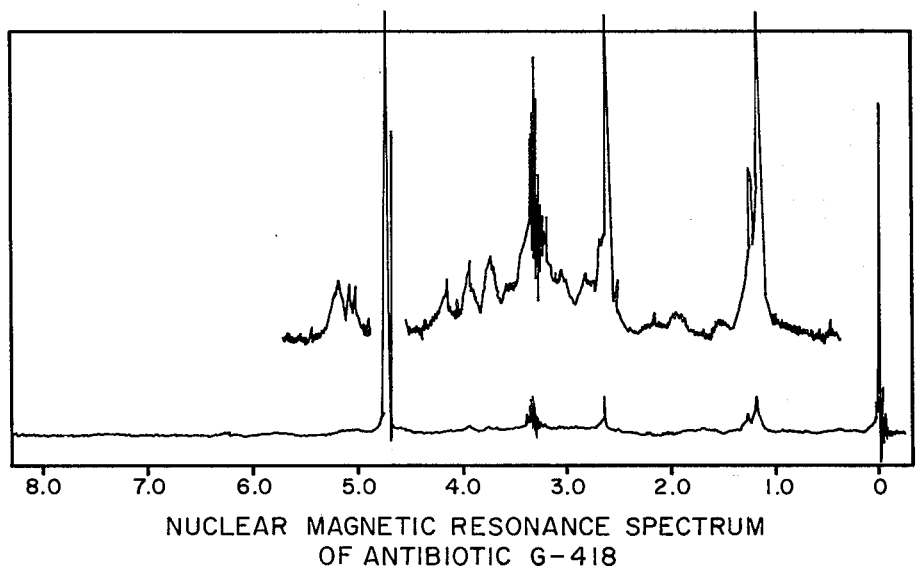

United States Patent [19]
Weinstein et al.

[11] 3,959,254
[45] May 25, 1976

[54] ANTIBIOTIC G-418 AND THE PRODUCTION THEREOF

[75] Inventors: Marvin J. Weinstein; Gerald H. Wagman, both of East Brunswick; Raymond T. Testa, Verona; Joseph A. Marquez, Montclair, all of N.J.

[73] Assignee: Schering Corporation, Kenilworth, N.J.

[22] Filed: Nov. 8, 1973

[21] Appl. No.: 414,010

Related U.S. Application Data

[63] Continuation-in-part of Ser. No. 196,707, Nov. 8, 1971, abandoned.

[52] U.S. Cl............................ 260/210 AB; 195/96; 424/181
[51] Int. Cl.².................................... C07H 15/22

[58] Field of Search................... 260/210 AB, 210 R

[56] References Cited
UNITED STATES PATENTS
3,651,042    3/1972    Marquez et al. ............. 260/210 AB

*Primary Examiner*—Johnnie R. Brown
*Attorney, Agent, or Firm*—Carver C. Joyner; Raymond A. McDonald; Stephen B. Coan

[57] ABSTRACT

A novel actinomycete herein designated *Micromonospora rhodorangea* elaborates a product having substantial antibacterial activity, said activity being due primarily to a novel antibiotic herein designated Antibiotic G-418. The disclosure sets forth methods for producing, isolating and using said antibiotic.

5 Claims, 2 Drawing Figures

NUCLEAR MAGNETIC RESONANCE SPECTRUM
OF ANTIBIOTIC G-418

INFRARED SPECTRUM OF
ANTIBIOTIC G-418

ANTIBIOTIC G-418 AND THE PRODUCTION THEREOF

This application is a continuation-in-part of our co-pending application Ser. No. 196,707, filed Nov. 8, 1971, now abandoned.

This application relates to the cultivation of a novel actinomycete and to the novel product elaborated thereby. More particularly, this application relates to a new species of *Micromonospora* herein designated *Micromonospora rhodorangea* (sometimes referred to as *Micromonospora* G-418) and also relates to a novel antibiotic substance herein designated Antibiotic G-418.

Antibiotic G-418 and its pharmaceutically acceptable derivatives exhibit the applied use characteristic of adversely affecting the growth of gram-positive and gram-negative microorganisms. Further, Antibiotic G-418 and said pharmaceutically acceptable derivatives also adversely affect the growth of cultures of protozoa, especially parasitic protozoa such as *Trichomonas vaginalis* and *Entamoeba histolytica*. Moreover, Antibiotic G-418 and said pharmaceuticaly acceptable derivatives also adversely affect the growth of helminths such as *Syphacia obvelata* and *Hymenolepsis nana*. In exhibiting each of the foregoing applied use characteristics Antibiotic G-418 and its pharmaceutically acceptable derivatives may be utilized under in vivo or under in vitro conditions. Thus, Antibiotic G-418 may be used to inhibit or destroy susceptible species of the above-described organisms; and in conjunction with soaps and detergents, remove such organisms from the surfaces of laboratory equipment, surgical intruments, laboratory glassware and the like. In view of their in vivo action, Antibiotic G-418 its pharmaceutically acceptable derivatives may be used to destroy or inhibit susceptible organisms within mammalian hosts, such as mice, rats, cats, dogs, cattle and the like. As used herein the term pharmaceutically acceptable derivatives embraces principally, but not exclusively, acid addition salts and Schiff base-oxazolidine derivatives of Antibiotic G-418.

THE MICROORGANISM

*Micromonospora* G-418 described herein has been classified as a new species of *Micromonospora* based upon its taxonomical and growth properties on a number of standard agar media. On such media, the colonies have a red-orange appearance. Thus, we have designated the microorganism *Micromonospora rhodorangea*, the production of Antibiotic G-418 being a characteristic of this species. *Micromonospora rhodorangea* has been deposited at the Northern Utilization Research and Development Division, U.S. Department of Agriculture, Peoria, Ill. and added to its collection of microorganisms as NRRL 5326.

The microorganism has the microscopic, macroscopic and biochemical properties set forth below.

1. TAXONOMY a. Macroscopic observations of 30 day old culture incubated at 24°–26°C on a 3% NZ Amine Type A, 1% dextrose and 1.5% Agar medium shows poor growth with no visible distinguishing characteristics.

b. Microscopic observations of the same culture shows the mycelium to about 0.4–0.8 μm in diameter and sparsely branched. Chlamydospores are occasionally observed, however, no true spores are observed. Thus, the species appears to be a non-sporulating one.

1. Observations on Emerson's agar, Bennetts Agar, yeast extract-dextorse agar and starch agar are substantially the same as described in (b).

In the following descriptions of the microorganisms two color designates are used. The first is taken from the "Color Harmony Manual," 4th Edition 1958, published by the Container Corporation of America (U.S.A.) and the description for the first designate is taken from the "Descriptive Color Name Dictionary" by Taylor, Knoche and Granville also published by the Container Corporation of America (1950). The second color designate is a synonym or near synonym of the first and is taken from the National Bureau of Standards Circular No. 553 (1955) U.S.A.

TABLE I

COLONY OBSERVATIONS OF MICROMONOSPORA G-418 ON VARIOUS MEDIA

| Medium | Observation |
|---|---|
| Glucose Asparagine Agar | no growth |
| Gelatin | weakly liquefied |
| Milk | growth good, hydrolysis complete, colony plicate, g6pa brite coral red, vivid reddish orange 34 |
| Sucrose | utilized |
| Starch | growth good, hydrolysis complete |
| Cellulose | decomposed |
| Nitrate Reduction | positive |
| Temperature | grows well at 28°C, growth fair to poor at 37°C, no growth at 45°C or above |
| Aerobic or Anaerobic | aerobic |
| Czapek's Sucrose Agar (Difco) | growth poor, flat, color: g7pl burgandy, dark grayish, reddish brown-47 |
| Bennett's Agar | growth good, plicate, membranous, no aerial mycelium, no diffusible pigment, color g6pg chinese red, deep reddish orange 36 |
| Tomato paste Oatmeal, Agar | growth poor, not recordable |
| Glucose Yeast extract Agar | growth moderate, membranous, no aerial mycelium, no diffusible pigment, color g6pg barn red, mode reddish brown 43 |
| Potato slice | no growth |
| Sucrose Nitrate Agar (Czepek's Agar) | growth poor, flat, g 7½ pi dark wine, dark reddish brown-44 |
| Tyrosine Agar | Tyrosine yeast — growth good, plicate, crystals dissolved, dark amber diffusible pigment |
| Observations at 2,7 and 14 days (after Gordon and Smith J. Bact. (69:147) | Tyrosine beef — growth poor, flat, crystals, not dissolved, slight amber diffusible pigment |
| Peptone Iron Agar Observations at 2,7 and 14 days | no growth |
| Bromo cresol purple milk | completely peptonized, dark maroon |

Table II sets forth carbohydrate utilization data for *Micromonospora* G-418

TABLE II

CARBOHYDRATE UTILIZATION

| Carbohydrate | Observation |
|---|---|
| Arabinose | growth moderate |
| Cellulose | growth fair |
| Glucose | growth good |
| Galactose | growth fair |
| Lactose | growth fair |
| Levulose | growth poor |
| Mannose | growth good |
| Raffinose | growth poor |
| Rhamnose | growth poor |

TABLE II-continued

| CARBOHYDRATE UTILIZATION | |
|---|---|
| Carbohydrate | Observation |
| Starch | growth good |
| Sucrose | growth good |
| Xylose | growth good |
| Inositol | growth poor |
| Mannitol | growth poor |
| Sorbitol | growth poor |
| Control 0.5% yeast extract | growth poor |

Table III sets forth nitrogen utilization data for *Micromonospora* G-418

TABLE III

UTILIZATION OF NITROGEN SOURCES

| Nitrogen Sources +1% glucose | Observation |
|---|---|
| 0.5% Difco Yeast Extract | growth moderate, membranous, no aerial mycelium no diffusible pigment, color g 6½ pg barn red, deep reddish brown-41 |
| 1.0% NZ Amine Type A | growth fair, flat, furrowed, no aerial mycelium no diffusible pigment, g6pc chinese red, deep reddish orange-36 |
| 1% Asparagine | growth poor, flat, no aerial mycelium, no diffusible pigment, g6pi brown mahogany, deep reddish brown-41 |
| 1% Glutamic Acid | growth poor, flat, no aerial mycelium no diffusible pigment, color g7pi dark wine, dark reddish brown-44 |
| 1% Sodium Nitrate | no growth |
| 1% Ammonium Nitrate | no growth |

PRODUCTION OF ANTIBIOTIC G-418

*Micromonospora* G-418 produces Antibiotic G-418 when cultivated in a nutrient medium containing assimilable sources of carbon and nitrogen. Substantial quantities of the antibiotic are produced when the microorganism is cultivated in an aqueous nutrient medium under submerged aerobic conditions. Exemplary of assimilable carbon sources are carbohydrates, such as, those set forth in Table II, especially glucose, xylose, and mannose. Exemplary of assimilable sources of nitrogen are proteins, amino acids and substances containing the same such as, beef extract, yeast extract, soybean meal, and the like. Specific examples of such nitrogen sources are set forth in Table III. Good growth and antibiotic production may be obtained using the fermentation procedures set forth in the specific examples. The media may be supplemented with trace amounts of inorganic salts such as magnesium sulfate, ferrous sulfate, and especially, cobalt chloride to enhance antibiotic production. In general, the fermentation is conducted at a temperature range of from about 25°–35°C with continuous agitation at from about 250–400 rpm. Under these conditions, peak antibiotic product is attained in from about 2 to about 4 days.

Generally, the fermentation is carried out in two or more stages, there being one or more germination stages followed by a fermentation stage. As a general rule, large (tank) fermentations utilize two germination stages whereas shake flask fermentations utilize a single germination stage.

During the course of the fermentation especially after the first 24 hours, the fermentation is assayed at convenient intervals (e.g. every 6 to 8 hours), to determine when peak production is reached.

MICROBIOLOGICAL ASSAY

The assay is a standard disc plate assay using Difco Antibiotic Medium No. 5 and *Bacillus subtilis* A.T.C.C. 6633 as the test organism. The physical conditions of the test are substantially those described for neomycin (Grove and Randall), Assay Methods of Antibiotics published by Medical Encyclopedia Incorporated (1955). The assay is run against a standard preparation of Antibiotic G-418 having a defined potency of 1000 mcg/mg. One microgram of the standard gives a zone of inhibition of 16.5 ± 1.5 mm in the test. The standard antibiotic sulfate salt assays about 750 mcg/mg. against the standard antibiotic base.

When peak antibiotic activity is attained, the product is harvested, generally, by a combination of steps such as acidification, filtration, adsorption, elution, lyophilization and the like. In a preferred isolation procedure, the whole broth is acidified preferably with a mineral acid and the fermentation mixture clarified by filtration or centrifugation. After neutralization, the antibiotic product is adsorbed upon a suitable cation exchange resin, eluted with dilute alkali, preferably ammonium hydroxide and isolated by lyophilization.

The product obtained by the foregoing procedure contains substantially the entire complement of antibiotics produced by the fermentation.

By subjecting the crude lyophilizate to chromatography and bioautography, a plurality of zones of inhibition are observed. For example, using a chromatographic system consisting of 2-butanone-tertiary butanol-methanol-concentrated ammonia in the ratio of 16:3:1:6 (v/v) on Whatman No. 4 paper, descending overnight (16hours), one major and about five minor products are detected by bioautography against *Staphylococcus aureus* ATCC 6538P. Antibiotic G-418 (the major product) is the least polar of the group.

THE ANTIBIOTIC

From the following physicochemical data it is believed that Antibiotic G-418 has the gross (flat) structure depicted by Formula IA and has the stereochemical formula depicted by Formula IB below:

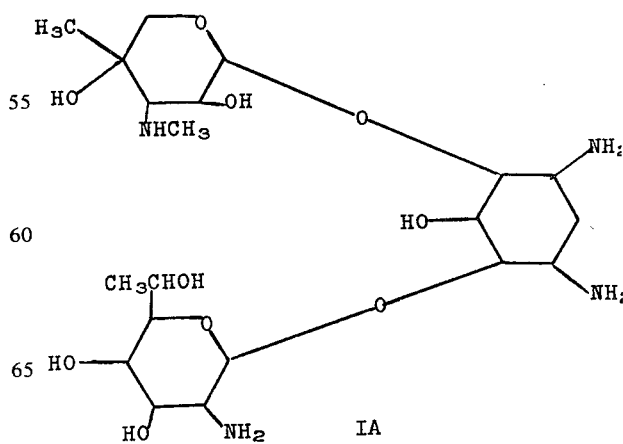

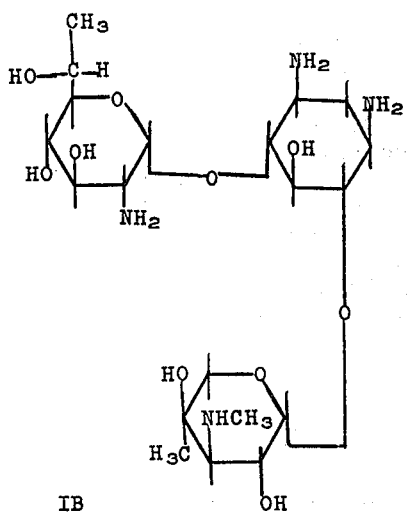

IB

Antibiotic G-418 is an aminoglycoside antibiotic and, therefore, belongs to the class that includes gentamicin, neomycin, paromomycin, sisomicin, kanamycin and the like. It is usually isolated in the form of an amorphous white solid having the following physical constants: m.p. 138°–144°C; Rotation: +140°± 9° (C=0.3%, H₂O); Molecular Weight (Mass spectometry) = 497; Empirical Formula: $C_{20}H_{40}O_{10}N_4$ (base) $C_{20}H_{40}O_{10}N_4 \cdot 2H_2SO_4$ (sulfate).

N.M.R. — Substantially as shown in FIG. 1, which was obtained from a solution containing 15% of Antibiotic G-418 in deuteriomethanol with 3% tetramethylsilane added as the internal reference.

Figure 2:
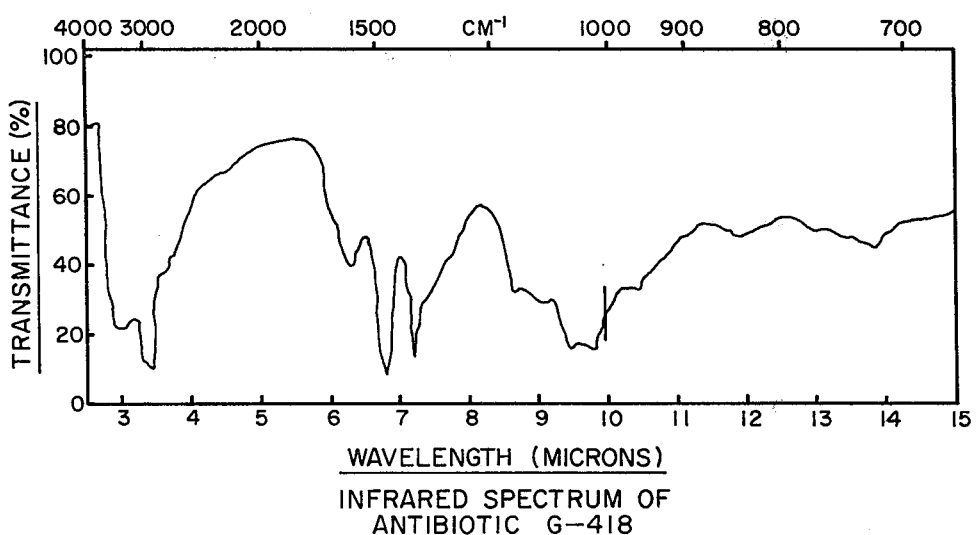

I.R. — Is a Nujol mull substantially as shown in FIG. 2, which has characteristic absorption bands as follows:

| | | |
|---|---|---|
| 3.02 μ (S) | 9.07 μ (S) | 11.86 μ (W) |
| 6.32 μ (M) | 9.49 μ (S) | 13.05 μ (W) |
| 7.76 μ (W) | 9.77 μ (S) | 13.87 μ (W) |
| 8.70 μ (M) | 10.42 μ (M) | |

(S) = Strong, (M) = Medium, (W) = Weak.

The pharmaceutically acceptable acid addition salts of Antibiotic G-418 previously referred to are generally prepared by titrating the free nitrogen base with acid. The salt is advantageously isolated by precipitation from an aqueous solution by a water miscible organic solvent, preferably a lower alcohol. Such salts are generally derived from inorganic acids, such as the mineral acids, and from hydrocarbon carboxylic acids such as the aliphatic acids including straight chain branched chain and cyclic aliphatic acids; aromatic hydrocarbon carboxylic acids and aralkyl carboxylic acids. Exemplary of such acids are sulfuric, hydrochloric, phosphoric, cyclopropanecarboxylic, adamantane carboxylic, benzoic, pivalic, phenylacetic, acetic, propionic, caproic, stearic and oleic acids.

Similarly, the pharmaceutically acceptable Schiff base-oxazolidine derivatives of Antibiotic G-418 are generally prepared by treating an alcoholic solution of the antibiotic free nitrogen base with an excess of aldehyde above ambient temperature for about one hour, chilling the solution to obtain the desired product, usually in the form of a crystalline solid. As can be seen from formula I, the antibiotic has three primary amino groups, each of which can form a Schiff base. Further the antibiotic has a secondary amino group vicinal to a tertiary hydroxy group which combination with aldehyde, gives rise to an oxazolidine derivative. Thus when the antibiotic is reacted with an excess of aldehyde, four moles of aldehyde react with each mole of antibiotic to yield the Schiff base-oxazolidine derivative which for convenience is depicted by formula II in the planar form.

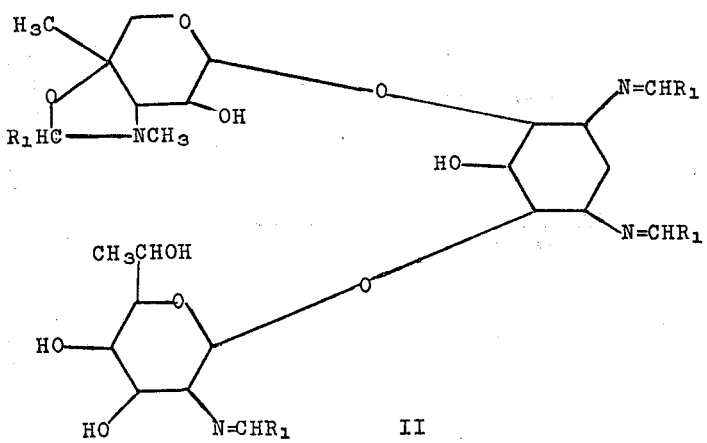

wherein R₁CH= is an alkylidene radical containing 2 to 12 carbon atoms; a cycloalkylidene radical containing 4 to 12 carbon atoms; an aralkylidene radical containing 7 to 12 carbon atoms; or an aromatic-heterocyclic containing 6 to 12 carbon atoms.

Representative of various aldehydes which upon reaction with the antibiotic G-418 so as to provide a derivative of formula II are: acetaldehyde, propionaldehyde, butraldehyde, crotonaldehyde, furfural, cyclopentylacetaldehyde, vanillin, veratraldehyde, benzaldehyde, p-nitro-benzaldehyde, salicylaldehyde, pyridoxal and the like.

These Schiff base-oxazolidine derivatives are not appreciably soluble in water but are soluble in most commonly used organic solvents such as chloroform, methanol, acetone, ethyl acetate and the like. Further, these derivatives are unstable in organic solvents containing traces of water and will revert to the free antibiotic. The presence of a trace amount of acid facilitates the reversion.

In Table IV and Table V are set forth the in vitro antibacterial spectrum of Antibiotic G-418 against a variety of gram-positive and gram-negative bacteria using standard art recognized methods.

Table IV

Biological Properties of Antibiotic G-418
In Vitro Antibacterial Activity

| Organism | | MIC (mcg/ml)* |
|---|---|---|
| Staphylococcus aureus | 209P | 0.8 |
| | Gray | 7.5 |
| | Wood | 0.8 |
| | Ziegler | 0.8 |
| Streptococcus sp. | C | >25 |
| | C203 | 17.5 |
| Escherichia coli | Sc | 3.0 |
| | 894 | 7.5 |
| Klebsiella pneumoniae | DA20 | 3.0 |
| Pseudomonas aeruginosa | VA6 | 3.0 |
| | 37 | 17.5 |

*Minimum Inhibitory Concentration — Medium: Tryptose Phosphate Broth pH 7.2 – 7.5.

Table V

In Vitro Antibacterial Activity

| Organism | | MIC (mcg/ml)* |
|---|---|---|
| Bacillus subtilis | 6633 | 3.0 |
| Staphylococcus aureus | 12 | 3.0 |
| | 1257 | 0.3 |
| | Sm 1 | 0.3 |
| | 6 | 0.3 |
| | 23 | 0.3 |
| | 26 | 3.0 |
| | 32 | 7.5 |
| Streptococcus sp. | 30 | 7.5 |
| | 27 | 7.5 |
| | 16245 | 7.5 |
| | 6589 | 7.5 |
| | 3045 | 7.5 |
| Escherichia coli | 777 | 3.0 |
| | 887 | 3.0 |
| Pseudomonas aeruginosa | 1262 | 17.5 |
| | 1236 | 17.5 |
| | 20 | 3.0 |
| | 83 | 7.5 |
| Proteus mirabilis | 12453 | 7.5 |
| morganii | 8019 | 0.8 |
| rettgeri | 9250 | 0.3 |

*Mueller — Hinton Broth pH 7.2 – 7.5

In Table VI is set forth in vivo antibacterial data obtained with Antibiotic G-418. The host animals used to obtain the data were Carworth Farms CF-1 mice weighing about 18–20 g. In vivo protection ($PD_{50}$) is determined by injecting the mice (in groups of 7) intraperitoneally with a lethal dose of pathogenic bacteria. The mice are dosed with Antibiotic G-418 one hour later. The non-protected controls die in 18–24 hours whereas the survivors are alive 48 hours after infection when the test is terminated. The data is analyzed by standard probit procedures to determine $PD_{50}$ values with 95% confidence limits.

Table VI

In Vivo Antibacterial Activity of Antibiotic G-418
A. Protective Activity

| Organism | Route | $PD_{50}$ (mg/kg) |
|---|---|---|
| Staphylococcus aureus Gray | S.C. | 2.5 |
| | Oral | 40 |
| Eschericia coli Sc. | S.C. | 1.5 |
| Staphylococcus aureus St. M No. 1 | S.C. | 3.0 |
| Pseudomonas aeruginosa No. 1 | S.C. | 5.0 |

B. Acute Toxicity

| | Route | $LD_{50}$ (mg/kg) |
|---|---|---|
| | I.V. | 140 |

Table VII and Table VIII set forth in vivo test results which illustrate the antiprotozoal activity of Antibiotic G-418. The host for the tests were recently weaned male Royal Hart rats (3–4 weeks old) weighing about 50–70 g. The test procedure is a modification of one described by R. J. Schnitzer on pages 355–443 in Experimental Chemotherapy, Vol. 1, Academic Press, New York (1963).

Table VII

Oral Activity of Antibiotic G-418 and Reference Substances Against Experimental Cecal E. Histolytica Infections in Rats

| Preparation | Oral Dose mg/kg/day | Days Dosed | Parasitological Cure Negative/Total | A.D.I.* |
|---|---|---|---|---|
| Antibiotic G-418 | 25 | 6 | 19/19 | 0 |
| | 12.5 | 6 | 24/24 | 0 |
| | 10 | 3 | 7/7 | 0 |
| | 10 | 1 | 4/7 | 0.7 |
| | 6.5 | 6 | 4/4 | 0 |
| | 6.5 | 3 | 4/5 | 0.4 |
| | 6.5 | 1 | 2/5 | 1.0 |
| | 3.5 | 6 | 5/6 | 0.2 |
| | 3.5 | 3 | 0/7 | 1.7 |
| Paromomycin | 25 | 6 | 6/7 | 0 |
| | 12 | 6 | 4/8 | 0.8 |
| | 10 | 3 | 2/6 | 1.0 |
| | 10 | 1 | 0/7 | 2.1 |
| | 6.5 | 6 | 2/4 | 1.3 |
| | 6.5 | 3 | 1/5 | 1.0 |
| | 6.5 | 1 | 0/4 | 1.0 |
| | 3.5 | 6 | 1/6 | 1.5 |
| | 3.5 | 3 | 1/7 | 1.9 |
| Flagyl | 25 | 6 | 1/5 | 0.8 |
| | 13 | 6 | 2/6 | 0.8 |
| | 6.5 | 6 | 1/4 | 0.8 |
| | 6.5 | 3 | 0/3 | 1.7 |
| | 6.5 | 1 | 0/4 | 1.5 |
| Controls Dosed with water | | 6 | 4/45 | 2.2 |

*A.D.I. — defined as the average degree of infection based upon gross observations of pathological changes in the cecum and microscopic observations of the number of amoebae found. These observations are recorded on a scale of from zero to four, zero representing a substantially normal cecum. Untreated but infected controls range from about two to four. In the data set forth the controls averaged 2.2.

The following specific examples are set forth to describe the best mode of practicing this invention.

EXAMPLE 1

Tank Fermentation of *Micromonospora* G-418

A. First Germination Stage: To 1000 ml. of water add the following: beef extract 3 gm., tryptose 5 gm., yeast extract 5 gm., dextrose 1 gm., starch 24 gm., calcium carbonate 2 gm. Heat the mixture with agitation until the solids are either uniformly distributed and/or substantially dissolved. Divide the mixture into 10 equal parts (by volume) and transfer to 300 ml. shake flasks. Sterilize the medium at 121°C under 15 psi pressure for 20 minutes then cool the medium to about room temperature. Under sterile conditions, inoculate each flask with 5 ml. of a previously prepared whole broth preparation. Incubate the flasks at about 35°C with rotary agiation (300 rpm) for 3 days.

B. Second Germination Stage: To 500 ml. of sterile medium, prepared as described above, transfer asceptically 25 ml. of medium from the first germination stage and incubate at 28°C for 3 days with rotary agitation (300 rpm).

C. Fermentation: In a 14 liter fermentor, prepare 10 liters of fermentation medium having the following composition: soybean meal 350 gm., dextrin 500 gm., dextrose 50 gms., calcium carbonate 70 gm., cobalt chloride 130 mcg., and water 10 liters. Sterilize the fermentor and the medium at 121°C under 15 psi for 30 minutes then cool to about room temperature. Incubate the fermentation medium by adding 500 ml. of inoculum from the second germination stage under asceptic conditions. Conduct the fermentation at a temperature of about 35°C with the introduction of air at a rate of from about 2.5 to 5.0 liters per minute. Agitate the medium at a rate of from about 250 to 500 rpm. Continue the fermentation until peak activity is attained as determined by the previously described assay technique and workup as described in Example 2.

EXAMPLE 2

Isolation of Antibiotic G-418

To 20 liters of fermentation broth, add about 130 g. of oxalic acid with vigorous agitation. Adjust the pH of the broth to 2.0 with 6N sulfuric acid. Stir the mixture for about 30 minutes and filter. Wash the precipitate with enough tap water until the washes are substantially free of color. Combine the filtrate and washes and adjust the pH 7 with 6N ammonium hydroxide. Pass the combined filtrate and broth through an ion exchange resin column containing about 250 g. of IRC-50 in the ammonium form at a rate of from about 50 – 75 ml./minute. Wash the resin bed until the washes are color free and the antibiotic is eluted with 2N ammonium hydroxide. The eluate is concentrated in vacuo and lyophilized to yield about 5 gms. of crude antibiotic assaying about 105 mcg/mg. Paper chromatograph this crude antibiotic in a descending system composed of 2-butanone: tertbutanol:mthanol:conc. ammonium hydroxide (16:3:1:6), followed by bioautography against *Staphylococcus aureus* ATCC 6538P. (The bioautogram shows the product to containn substantially one spot with several barely visible minor spots.)

EXAMPLE 3

Partial Purification of Antibiotic G-418

Dissolve 4 gms. of Antibiotic G-418 as obtained from Example 2 in 100 ml. of water. Adjust the pH to 4.2 with 2N sulfuric acid, and add 250 mg. of activated charcoal (Darco G-60, Atlas Powder Co. Wilmington, Del.). Stir the suspension for about 1 hour, and filter. Concentrate the filtrate to about 50 ml. and precipitate into 500 ml. of methanol. Filter the resulting precipitate, wash with methanol and dissolve in about 20 ml. of water. Prepare a column of IRA-401S (an Amberlite anion exchange resin—Rohm and Haas, Philadelphia, Pa.) having substantially the following dimensions: height 65 cm.; inside diameter 25 cm.; resin 200 gms. Place the antibiotic solution atop the resin column and wash the solution through the column with deionized water. Concentrate the column effluent to about 20 ml. in vacuo and lyophilize to obtain from about 800 mg. to about 1.2 gms. of antibiotic G-418 assaying about 480 mcg/mg.

EXAMPLE 4

Purification of the Antibiotic Via Preparation of Antibiotic G-418 Sulfate

Dissolve 2.6 gms. of Antibiotic G-418, prepared according to Example 3, in 250 ml. of water and adjust the pH of the solution to 4.2 with dilute (1–6N) sulfuric acid. Add about 5 gms. of Darco G-60 to the solution and stir for about one hour at room temperature. Filter the suspension and concentrate the filtrate to dryness in vacuo. Dissolve the residue in 20 ml. of water and add dropwise to 500 ml. of methanol with vigorous agitation. Filter the resulting suspension, wash with methanol and dry at about 40°C in vacuo to obtain 3.36 gms. of Antibiotic G-418 sulfate assaying about 700 mcg/mg.

Similarly, by substituting sulfuric acid with an equivalent quantity of other inorganic or organic acids and by using acetone as the precipitation solvent, other functionally equivalent acid addition salts may be prepared.

EXAMPLE 5

Purification of the Antibiotic Via Resin Chromatography

Dissolve 300 mg. of Antibiotic G-418, prepared according to Example 3 in 20 ml. of deionized water. Prepare an ion exchange resin column having the following dimensions, height 25 cm.; outside diameter, 2 cm.; containing 20 g. of Dowex 1 × 2 resin in the hydroxyl form. Pass the antibiotic solution through the resin bed and elute with deionized water taking 3 ml. fractions. Combine the fractions containing the antibiotic activity (42–69), concentrate to about 10 ml. and lyophilize to obtain about 70 mg. of Antibiotic G-418 assaying 1000 mcg/mg.

We claim:

1. A compound selected from the group consisting of Antibiotic G-418 having the formula:

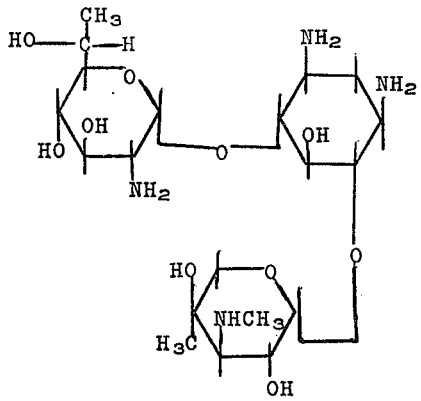

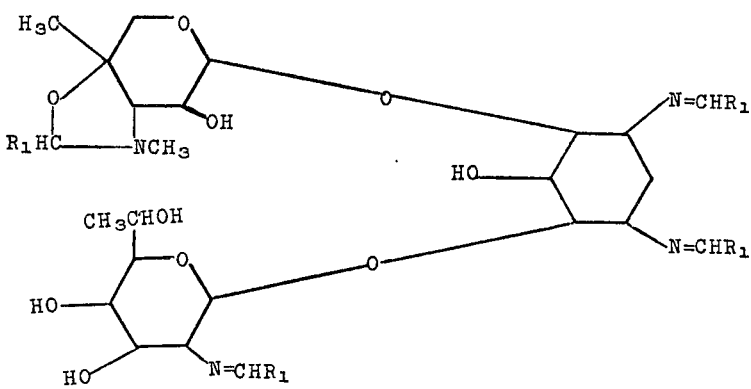

and the pharmaceutically acceptable acid addition salts thereof.

2. A compound of claim 1, said compound being Antibiotic G-418.

3. A compound of claim 1, said compound being an acid addition salt of Antibiotic G-418.

4. A compound of claim 3, said compound being Antibiotic G-418 sulfate.

5. A Schiff base-oxazolidine derivative of Antibiotic G-418 having the formula:

wherein $R_1C=$ is alkylidene containing 2 to 12 carbon atoms; cycloalkylidene containing 4 to 12 carbon atoms; aralkylidene containing 7 to 12 carbon atoms; or aromatic-heterocyclic containing 6 to 12 carbon atoms.

* * * * *